(12) United States Patent  
Beckers et al.

(10) Patent No.: US 9,110,003 B2
(45) Date of Patent: Aug. 18, 2015

(54) MICRODIFFRACTION

(71) Applicant: PANalytical B.V., Almelo (NL)

(72) Inventors: Detlef Beckers, Almelo (NL); Milen Gateshki, Almelo (NL)

(73) Assignee: PANALYTICAL B.V., Almelo (NL)

( * ) Notice: Subject to any disclaimer, the term of this patent is extended or adjusted under 35 U.S.C. 154(b) by 109 days.

(21) Appl. No.: 13/780,216

(22) Filed: Feb. 28, 2013

(65) Prior Publication Data

US 2013/0243159 A1 Sep. 19, 2013

(30) Foreign Application Priority Data

Feb. 28, 2012 (EP) .................................. 12157330

(51) Int. Cl.
*G01N 23/207* (2006.01)

(52) U.S. Cl.
CPC ........ *G01N 23/207* (2013.01); *G01N 2223/313* (2013.01)

(58) Field of Classification Search
CPC ... H01J 2229/0733; H01J 29/07; H01J 9/142; H01J 47/08; H01J 2237/1514; H01J 37/28; G01N 23/207; G01N 2223/313; G01N 2223/076; G01N 2291/02854; G01N 2291/0421; G01N 2291/0422; G01N 23/223; G01N 29/043; G01N 2223/40; G01N 23/20008; G01N 23/205; B41M 3/12
USPC ........................................... 378/71, 79
See application file for complete search history.

(56) References Cited

U.S. PATENT DOCUMENTS

| | | | |
|---|---|---|---|
| 7,123,686 B2 * | 10/2006 | Sakata ............................ | 378/71 |
| 2004/0156471 A1 | 8/2004 | Sakata et al. | |
| 2008/0084964 A1 * | 4/2008 | Dosho et al. .................... | 378/81 |
| 2011/0268251 A1 * | 11/2011 | He ................................. | 378/71 |

FOREIGN PATENT DOCUMENTS

| | | |
|---|---|---|
| DE | 38 39 990 | 6/1989 |
| JP | 2002 286660 | 10/2002 |
| WO | WO 99/60388 | 11/1999 |

* cited by examiner

*Primary Examiner* — Irakli Kiknadze
(74) *Attorney, Agent, or Firm* — Leason Ellis LLP

(57) ABSTRACT

A method of X-ray diffraction illuminates a beam (4) of X-rays along an illuminated strip (16) on a surface (14) of a sample (10). The X-rays are diffracted by the sample (10) and pass through a mask (20) having a slit extending essentially perpendicularly to the strip (16). The X-rays are detected by a two-dimensional X-ray detector to measure the diffracted X-rays at different positions along the strip (16).

10 Claims, 5 Drawing Sheets

MICRODIFFRACTION

FIELD OF INVENTION

The invention relates to a method and apparatus for X-ray diffraction.

BACKGROUND ART

X-ray diffraction is a well-known technique for materials analysis. In many applications, it is useful to carry out the materials analysis not merely at one spot on a sample, but at multiple points on a surface of the sample. This is particularly the case for samples which are not uniform crystals over their whole surface.

In such cases, it is generally necessary to carry out X-ray diffraction illuminating the sample with a very small spot to enable the diffraction to be measured at that spot. This gives rise to a number of difficulties. The spot is generally achieved using a pin-hole or other dedicated X-ray optics for microdiffraction which results in very low X-ray intensities. Further, in order to image other regions of the sample it is necessary to move the sample (or equivalently the spot) which requires accurate sample positioning possibilities (sample stage). This however is difficult especially at high resolutions where very accurate alignment of the sample may be required every time the sample is moved. Thus, measuring the X-ray diffraction across the surface of the sample can be a very difficult and time consuming job.

Accordingly, there is a need for an improved technique for measuring X-ray diffraction of samples.

SUMMARY OF INVENTION

According to the invention, there is provided a method of X-ray diffraction for measuring a sample having a sample surface, the method comprising:
a) illuminating a beam of X-rays along an illuminated strip extending along the surface of the sample in a y direction;
b) passing X-rays diffracted by the sample along the illuminated strip through a mask between the sample and a two-dimensional detector, the mask having a slit extending substantially perpendicularly to the y direction so that X-rays diffracted from different positions along the illuminated strip are received at different positions along the y direction on the two-dimensional X-ray detector; and
c) detecting X-rays diffracted by the sample at the two-dimensional X-ray detector, so that different positions along the y direction at the two-dimensional detector correspond to different positions along the illuminated strip and different positions in the perpendicular direction, z', to the line direction on the two-dimensional X-ray detector correspond to different diffraction angles 2θ.

By illuminating a strip on the sample, using a mask aligned in the correct direction and a two-dimensional X-ray detector, the X-ray diffraction pattern at multiple positions along the illuminated strip can be measured essentially simultaneously.

The illuminated strip may be generated using a source slit. The source slit may be moved to move the illuminated strip on the sample and hence to easily measure the X-ray diffraction pattern along different strips. Thus, the diffraction pattern across the surface of the sample in both x and y directions may be measured relatively easily. Alternatively, alternate collimating X-ray optics may be used.

The distance between the mask and the sample as a fraction of the distance between the sample and the two-dimensional X-ray detector may be varied to vary the length of the illuminated strip that is imaged by the two-dimensional X-ray detector.

The invention also relates to X-ray diffraction apparatus as claimed in claim 8, which is adapted to carry out the method as discussed above.

BRIEF DESCRIPTION OF DRAWINGS

For a better understanding of the invention, embodiments will now be described with reference to the accompanying drawings, in which.

The drawings are schematic and not to scale.

DETAILED DESCRIPTION

Figure 1:
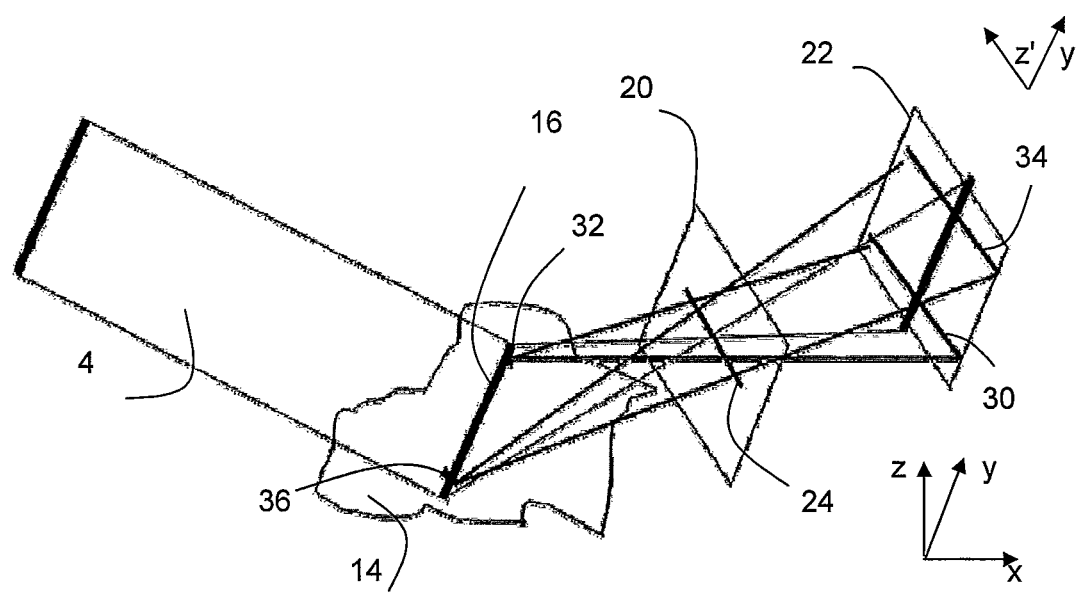
FIG. 1 is a perspective view of a first embodiment of the invention.
Figure 2:
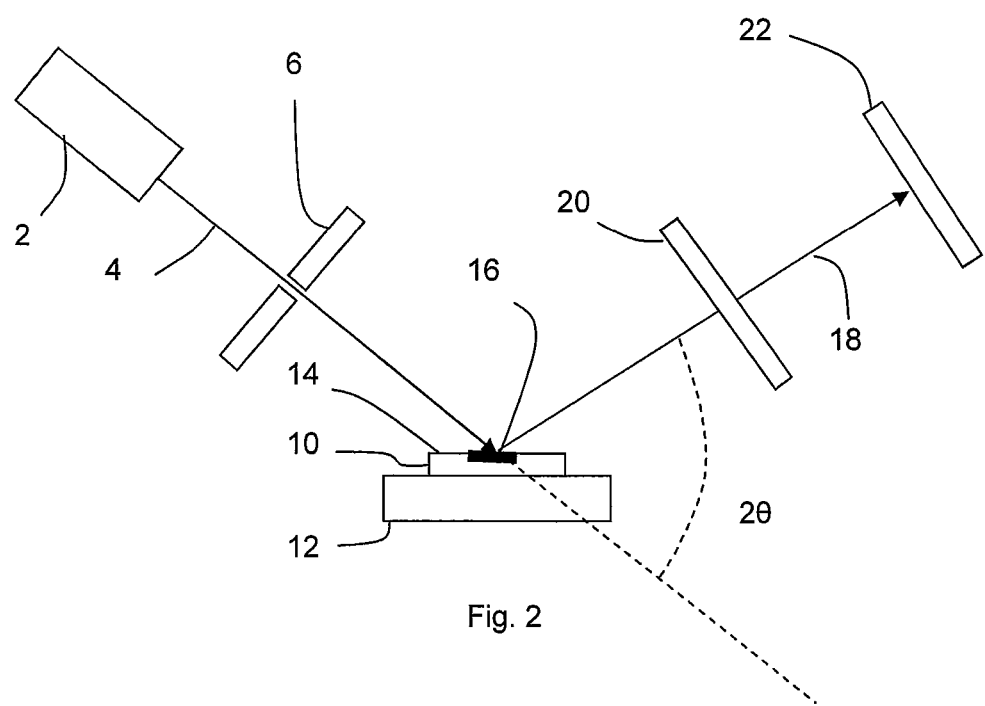
FIG. 2 is a side view of the arrangement of FIG. 1.

Referring to FIGS. 1 and 2, an X-ray source 2 is used to generate an X-ray beam 4 which passes through source slit 6. This generates an X-ray beam in the form of a sheet which illuminates the upper surface 14 of sample 10 on sample holder 12. A narrow source slit 6 is used to generate a narrow illuminated strip 16 of width w, the strip extending in the y direction and the width being in the x direction. In the embodiment, the width w is in the range 0.05 mm to 2 mm.

The X-rays incident on the illuminated strip 16 are diffracted by the sample 10 and form a diffracted beam 18 which passes through mask 20 to two-dimensional X-ray detector 22. The mask 20 has a slit 24 which extends in a perpendicular direction to the direction in which illuminated strip 16 extends, i.e. perpendicular to the y direction. The mask 20 is placed roughly halfway between the sample 10 and the X-ray detector 22, for example the mask 20 may be placed at a distance from the illuminated strip 16 of between 20% and 80% of the distance between the illuminated strip 16 and the X-ray detector 22.

As a result of this set up different regions of the X-ray detector 22 receive X-rays from different places along the length of the illuminated strip 16.

Consider line 30 on the X-ray detector. As may be seen from FIG. 1, all the X-rays incident on this line are from spot 32 towards one end of the illuminated strip. The detector pixel size and axial divergence (y-direction) of the X-ray beam determines how far the neighbourhood of spot 32 contributes to the signal detected in line 34—i.e. the effective resolution. Different positions along the length of line 30 correspond to different diffraction angles 2θ. Similarly, considering line 34 on the X-ray detector, this receives diffracted X-rays from spot 36 on the illuminated strip 16. Different positions along line 34 correspond to different diffraction angles 2θ.

Thus, the intensity information recorded on the two-dimensional X-ray detector 22 provides a plot in which variation along the y direction on the two-dimensional X-ray detector 22 corresponds to different positions along the y-direction in the illuminated strip 16. Variation along the z' direction on two-dimensional X-ray detector 22 corresponds to a plot of diffraction intensity at different angles 2θ.

In this way it is possible to simultaneously obtain data from multiple spots on the sample along the illuminated strip. This can result in fast micro-diffraction analysis without the need to move the sample in y-direction. In addition it is possible— by simple integration of the intensity of neighbouring pixels of the 2D detector (in y-direction) to optimize between the effective spot resolution and collected intensity from that sample area (without the need for adoption of the optics).

Further, it is not necessary to align the sample accurately in the y-direction. Accurate alignment can be a difficult and time consuming process and avoiding the need for this can greatly improve the experimental set-up time.

The mask slit should be oriented within the diffraction plane (along the 2θ direction, preferably as accurately as possible. This will minimise smearing out of the measurement result on the detector when it is moving—resulting in bad resolution. The orientation of the illuminated strip on the sample is less critical—it can be slightly tilted. If the geometry is known the corresponding 2θ angles can be corrected.

The size of slit 24 in mask 20 can be changed as can the size of source slit 6. These can be adjusted in particular to optimise the recorded intensity and spot resolution. The resolution in the y-direction is controlled by the slit 24 and the spot resolution on the sample in x-direction by the width of the source slit 6. In addition, the axial divergence of the X-ray beam (divergence in y-direction) and the detector pixel size influence the achievable spot resolution on the sample as well as the 2θ resolution of the recorded data. Additional Soller slits can be placed between source 2 and sample 10 (either before or after the slit 6) to limit the axial divergence (divergence in y-direction) of the X-ray beam 4. A smaller axial divergence will improve as well the spot resolution as also the 2θ resolution of the recorded data.

The distance between mask 20 and detector 22 can be adjusted to magnify or reduce the pattern on detector 22. When the mask is placed closer to the detector, the detector images a longer length of the illuminated strip 16, and when the mask is moved away from the detector the detector images a shorter length of the illuminated strip 16.

No dedicated micro-optics are required.

No sample movement in the y-direction is required to image different spots on the sample. This can result in a cheaper sample stage 12.

Further, if the source slit 6 can be moved to illuminate different regions of the sample in the x-direction, there is no need to move the sample in the x-direction either. Thus, in this case it is possible to implement the invention in apparatus in which the sample stage does not require controlled motion in either the x-direction or the y-direction to achieve results across the surface of the sample.

The diffractometer can be used in line focus mode and there is no need to reduce the illumination of the sample to a point focus. In this way, the flux of the X-rays can be much larger than with a point focus arrangement.

In alternative embodiments, further beam optics can be used on the source side such as collimators and the like to achieve even greater control of the width of the illuminated strip 16 on the sample. In this way, widths w as low as 0.05 mm may be achieved.

The set up has been tested and measurement results will now be presented.

For the measurements, the system was configured with a source slit 6 that created a 0.5 mm wide illuminated strip and 0.04 radian Soller slits. The sample stage was fixed and the sample clamped in. A PIXcel$^{3D}$™ detector was used as the detector. As the mask 20, masks with a slit width of 0.25 mm, 0.15 mm and 0.05 mm were mounted in a fixed holder at approximately half the distance between the sample and detector.

Figure 3:
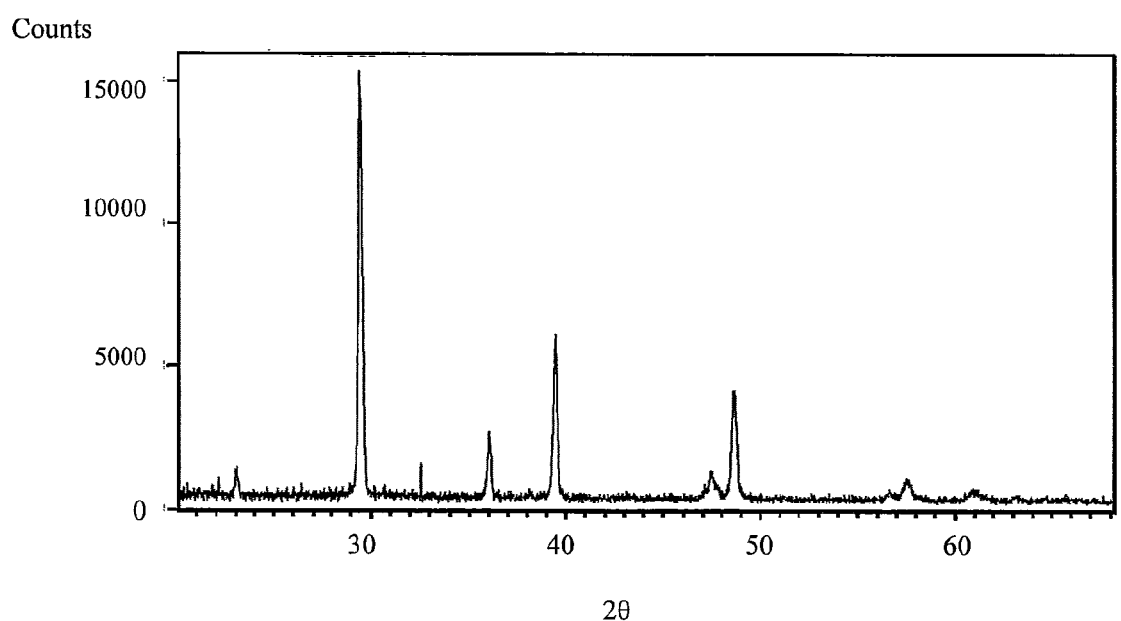
FIG. 3 shows results obtained using the invention.

Scans were carried out with the described set-up. A 1D graph created with integration of 10 neighbouring pixels (width of 55 µm per pixel) is shown in FIG. 3. Depending on the used mask size this corresponds to a spot resolution on the sample (x, y) between 0.5 mm×0.65 mm (0.05 mm mask) and 0.5 mm×1.05 mm (0.25 mm mask). The graph in FIG. 3 shows the counts (intensity value) against 20. For higher spatial resolution in y-direction on the sample it is simply possible to integrate less neighbouring pixels.

Figure 4:
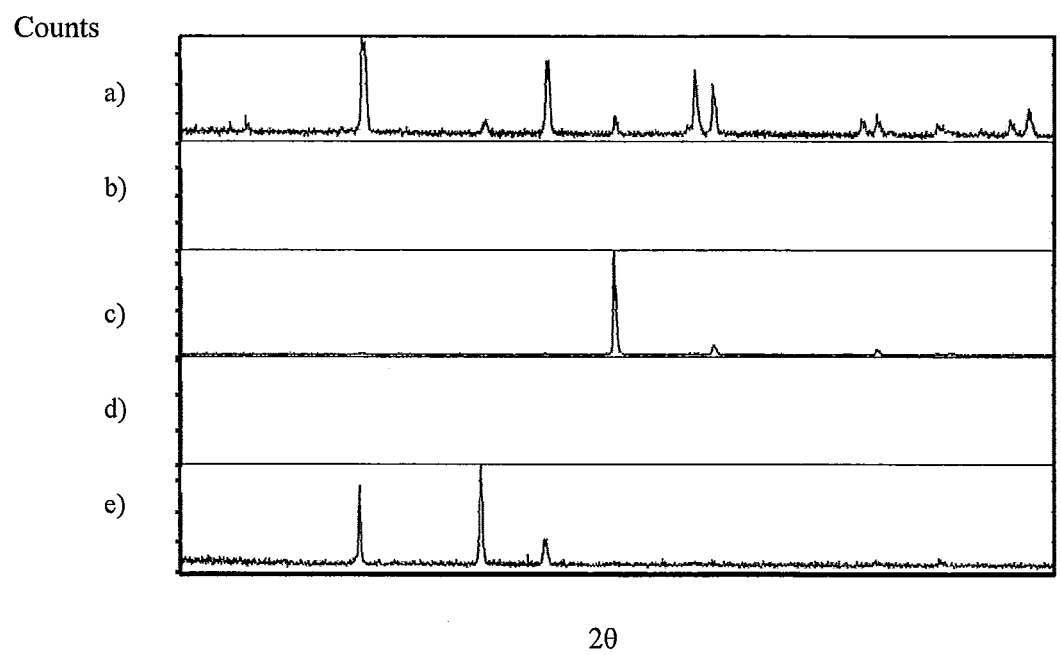
FIG. 4 shows a photomicrograph.

FIG. 4 is a photomicrograph showing diffraction patterns as a function of 2θ at different positions across the edge of the detector—i.e. each graph is a graph of intensity (counts) along a line in the z' direction in FIG. 1, and the different graphs are different lines 30,34 in FIG. 1, i.e. displaced along the y axis. Compositional variation along the line may be seen.

Figure 5:
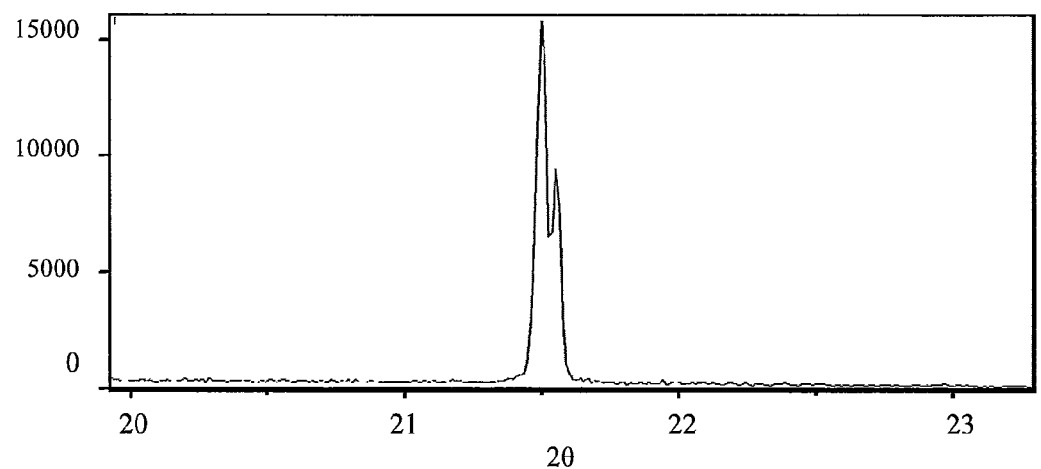
FIGS. 5 and 6 show results using a parabolic and an elliptical mirror.
Figure 6:
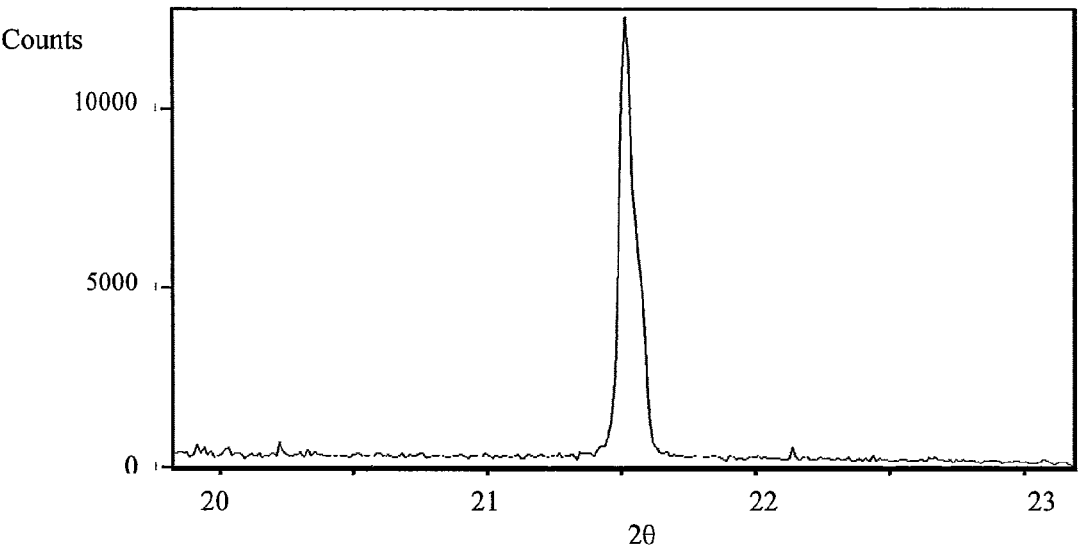

Additional tests were carried out with different incident beam Soller slits and with both parabolic and elliptical mirrors on the source side. These experiments showed that the parabolic mirror delivered slightly better angular resolution and was able to resolve doublets slightly better. The experiments measured a LaB$_6$ sample and were able to resolve the alpha ½ splitting of the reflection at 2θ=21.4 deg using a 0.1 mm source slit in front of the X-ray mirror which corresponds to approx. 0.17 mm beam width at the sample position (0.17 mm/sin θ illuminated stripe width) for the parabolic mirror and approx 0.10 mm beam width in case of the elliptical mirror (0.10 mm/sin θ illuminated stripe width)—or a 0.050 mm source slit which corresponds to 0.09 mm beam width for the parabolic mirror and approx 0.050 mm beam width in case of the elliptical mirror. FIGS. 5 and 6 show the peak measured using the 0.10 mm source slit with the parabolic mirror in FIG. 5 and the elliptical mirror in FIG. 6. The better resolution using the parabolic mirror is apparent—the doublet is better resolved in FIG. 5.

The invention is applicable to a range of samples. However, a particularly useful application is samples which are inhomogeneous over the surface. Within the spot size there should be sufficiently different grain orientations to get a reflection, as indeed is also the case for samples that are typically investigated in microdiffraction phase analysis experiments. Typical samples may be solid objects with heterogeneous grain/particle surface structure, but still with a relatively flat surface—e.g. geological samples, but also inhomogeneous pharmaceutical samples, concrete and others.

Compared with traditional microdiffraction which uses a pencil beam (narrow spot) instead of an illuminated strip, the X-rays detected at the edge of the detector are slightly shifted in 2θ, due to the different geometry. In the geometry described the observed shift of detected X-rays at the edge of the detector depends on the distance of the detector area to the centre of the detector (distance in y-direction), but also on the slit position (distance to detector and sample). If e.g. the slit is positioned in the middle between sample and detector, the observed 2θ shift corresponds to a shift that would be observed in a standard ("traditional") microdiffraction experiment at twice the distance from the detector middle.

These geometric effects can be corrected by calculation.

We claim:

1. A method of X-ray diffraction for measuring a sample having a sample surface, the method comprising:
   illuminating a beam of X-rays along an illuminated strip extending along the surface of the sample in a y direction;
   passing X-rays diffracted by the sample along the illuminated strip through a mask between the sample and a two-dimensional detector, wherein the mask has a slit extending substantially perpendicularly to the y direction and the mask is placed at a distance from the illuminated strip of between 20% and 80% of the distance between the illuminated strip and the X-ray detector so that X-rays diffracted from different positions along the illuminated strip are received at different positions along the y direction on the two-dimensional X-ray detector;

detecting X-rays diffracted by the sample at the two-dimensional X-ray detector, so that different positions along the y direction at the two-dimensional detector correspond to different positions along the illuminated strip and different positions in the perpendicular direction, z', to the line direction on the two-dimensional X-ray detector correspond to different diffraction angles 2θ.

2. The method according to claim 1, wherein the step of illuminating a beam comprises generating X-rays using an X-ray source and passing the generated X-rays through a source slit to illuminate the sample.

3. The method according to claim 2 further comprising moving the source slit to move the location of the illuminated strip on the surface of the sample.

4. The method according to claim 1 further comprising passing the beam through additional conditioning optics.

5. The method according to claim 1, wherein the sample is a sample with an inhomogeneous surface.

6. The method according to claim 1 further comprising adjusting the position of the mask to vary the length of the illuminated strip imaged by the two-dimensional X-ray detector.

7. The method according to claim 1 wherein the width of the illuminated strip (16) is 0.05 mm to 2 mm.

8. X-ray diffraction apparatus for measuring a sample having a sample surface, the apparatus comprising:
   an X-ray source for generating a beam of X-rays;
   a sample stage for supporting the sample;
   an X-ray optic between the X-ray source and the sample stage arranged to restrict the beam to illuminate an illuminated strip extending along the surface of the sample in a y direction;
   a two-dimensional X-ray detector for detecting X-rays diffracted by the sample; and
   a mask between the sample and the two-dimensional detector, wherein the mask has a slit extending substantially perpendicularly to the y direction and the mask is placed at a distance from the illuminated strip of between 20% and 80% of the distance between the illuminated strip and the X-ray detector so that X-rays diffracted from different positions along the illuminated strip are received at different positions along the y direction on the two-dimensional X-ray detector.

9. The X-ray diffraction apparatus according to claim 8 wherein the X-ray optic comprises a source slit (6).

10. A method of operation of X-ray diffraction apparatus:
   illuminating a beam of X-rays from an X-ray source passing through an X-ray optic along an illuminated strip extending along the surface of the sample in a y direction;
   passing X-rays diffracted by the sample along the illuminated strip through a slit in a mask so that X-rays diffracted from different positions along the illuminated strip are received at different positions along the y direction on a two-dimensional X-ray detector wherein the mask is placed at a distance from the illuminated strip of between 20% and 80% of the distance between the illuminated strip and the X-ray detector;
   detecting X-rays diffracted by the sample at the two-dimensional X-ray detector, so that different positions along the y direction at the two-dimensional detector correspond to different positions along the illuminated strip and different positions in the perpendicular direction, z', to the line direction on the two-dimensional X-ray detector correspond to different diffraction angles 2θ.

* * * * *